United States Patent [19]

Silverstein et al.

[11] Patent Number: 5,178,150

[45] Date of Patent: Jan. 12, 1993

[54] MINIATURE ULTRASOUND IMAGING PROBE

[76] Inventors: Fred E. Silverstein, 1246 - 15th Ave. E., Seattle, Wash. 98112; Andrew H. Proctor, 32527 NE. 120th St., Duvall, Wash. 98019

[21] Appl. No.: 660,525

[22] Filed: Feb. 25, 1991

[51] Int. Cl.$^5$ .............................................. A61B 8/12
[52] U.S. Cl. ............................ 128/662.06; 128/660.1
[58] Field of Search ...................... 128/662.03–662.06, 128/660.03; 604/96–103

[56] References Cited

U.S. PATENT DOCUMENTS 4,375,818  3/1983  Suwaki et al. ................... 128/662.06

OTHER PUBLICATIONS

*Endoluminal US: Experiments with Nonvascualr Uses in Animals* by Barry B. Goldberg, M.D., Ji-Bin Liu, M.D., Daniel A. Merton, B.S., R.D.M.S. & Alfred B. Kurtz, M.D. Genitourianary Radiology, vol. 175, No. 1, Apr. 1990.

Utsugi, M. "Ultrasonic Diagnostic Apparatus for Examination of the Cocliac Cavity", EP 0062315 published Oct. 13, 1982.

Taylor, W. B. et al., "A High-Resolution Transrectal Ultrasonographic System", Uts in Med & Biology, vol. 5, 1979, pp. 129–138.

*Primary Examiner*—Francis Jaworski
*Attorney, Agent, or Firm*—Seed and Berry

[57] ABSTRACT

A miniature ultrasound imaging probe that may be delivered through the biopsy channel of an endoscope. The probe includes a probe tip mounted at the distal end of a flexible catheter. The probe tip includes a transducer body mounted on the distal end of a distal actuating rod with the transducer body carrying an ultrasound transducer. The distal actuating rod is mounted on the distal end of a plurality of concentric, springs wound in opposite directions extending concentrically through the catheter and terminating in a proximal actuating rod. A flexible bag filled with an acoustic coupling fluid is mounted at the distal end of the catheter. The bag surrounds the transducer body to isolate it from the external environment and retain the acoustic coupling fluid. When the probe is to be inserted through a narrow passage, the proximal actuating rod is advanced into the catheter to extend the transducer body against the flexible bag. As a result, the bag elongates and its width is reduced. When the probe is to be used for imaging, the proximal actuating rod is retracted to withdraw the transducer body away from the bag and allow the bag to expand radially so that it can conform to a surface through which an image is to be obtained.

26 Claims, 3 Drawing Sheets

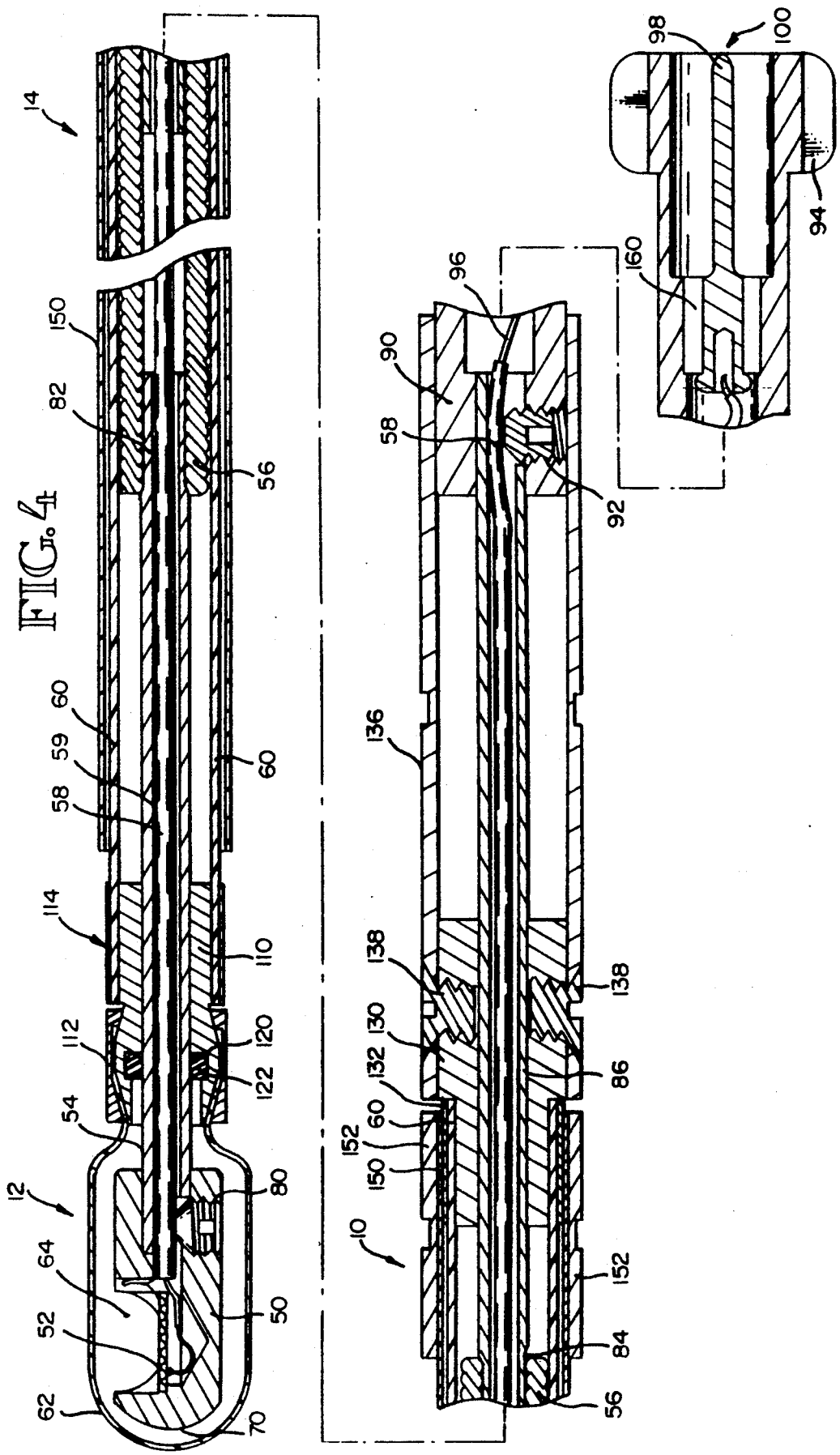

MINIATURE ULTRASOUND IMAGING PROBE

DESCRIPTION

1. Field of the Invention

This invention relates to ultrasound imaging, and more particularly to a miniature ultrasound imaging probe that may be inserted through the biopsy channel of an endoscope to endoscopically image internal organs.

2. Background Art

Ultrasound imaging is commonly used in the field of medicine to diagnose various types of medical disorders. These ultrasound imaging systems include an electronics unit connected to an ultrasound probe containing an ultrasound transducer which is placed in contact with tissues in the area of interest. The electronics unit generates high frequency electrical signals that are applied to the transducer to cause it to generate corresponding ultrasound signals. The ultrasound signals propagate through underlying tissues and/or blood vessels and are reflected from tissues or moving sound scatters in blood vessels. The reflected ultrasound signals propagate through tissues back to the ultrasound transducer where they are converted to corresponding electrical signals. The electrical signals are applied to the electronics unit which displays an image of the tissues and/or blood flow on the basis of the intensity and timing of the reflected ultrasound signals.

Ultrasound systems for imaging blood flow generally utilize the Doppler principle to reject reflections from stationary tissues while processing reflections only from moving sound scatterers such as flowing blood in veins and arteries. Ultrasound systems for imaging tissue utilize reflections generated by discontinuities in tissues formed by different layers of tissues, the walls of various organs, tumors or the like. Ultrasound signals are also reflected from the boundary between the transducer and the underlying tissue if good acoustic coupling is not provided between the transducer and the underlying tissue. In particular, it is important that there be no spacing or air gaps between the transducer and the tissue. However, it is often necessary to image through curved or irregular tissue surfaces, thus making it difficult for the entire surface of the transducer to be in contract with tissue surface. For this reason, a coupling gel or compliant coupling member is often placed between transducers and the surfaces of tissues to be imaged.

Ultrasound imaging is frequently accomplished externally by manually placing a transducer against the skin of a patient adjacent the tissue or organ of interest. However, it is often desirable to obtain ultrasound images internally. Internal ultrasound imaging can be accomplished using an ultrasound imaging system having an electronics unit connected to a miniature transducer by a thin, flexible catheter. The distal end of the catheter on which the ultrasound transducer is mounted is inserted through the biopsy channel of an endoscope after the endoscope has been inserted into an internal organ. The endoscope is then manipulated to place the transducer against the surface of the tissue or organ of interest, and the transducer is used to scan either linearly or radially. The position of the transducer is measured, and this position is used along with the ultrasound reflections to generate an ultrasound image in the electronics unit.

Ultrasound imaging through the biopsy channel of an endoscope creates a number of problems that are not present in external ultrasound imaging. The surface of the tissues or organs of interest are often curved or irregular, thus making it difficult for the transducer to flushly contact the surface to ensure good acoustic coupling. Further, unlike external ultrasound imaging where the transducer can be directly manipulated, endoscopically delivered ultrasound transducers can be manipulated only indirectly by either moving the probe in and out of the endoscope channel, rotating the probe tip or moving the distal end of the endoscope. As a result, it is even more difficult to keep the transducer flushly contacting the surface to ensure good acoustic coupling. This difficulty is exacerbated by the need to scan the transducer across the underlying surface.

Not only is it difficult to keep an endoscopically delivered transducer flush with the surface of interest, but the acoustic coupling gels that can provide external ultrasound transducers with good acoustic coupling generally cannot be used for internal imaging. First, internal consumption of acoustic coupling gels is generally not advisable. Second, delivery of the gel to the area of imaging interest may be difficult if the endoscope used has only one channel. Third, even if it was possible to place a layer of coupling gel on the surface of interest, it is doubtful that the gel would remain in position particularly after substantial scanning of the transducer or if the target is in a non-dependent position in which case the gel will tend to slip out from between the transducer and tissue. The gel may also be displaced by gravity when placed on a non-horizontal surface, and by internal body fluids.

Acoustic coupling members that can be used to provide external ultrasound transducers with good acoustic coupling are also generally unsuitable for use with an endoscopically delivered transducer. Acoustic coupling members must be capable of conforming to curved and irregular surfaces, and they should be able to remain flush with a surface even if the active surface of the transducer is not exactly parallel to the surface of interest. For this reason, acoustic coupling members must be relatively large and compliant. It is difficult to make even the transducer sufficiently small to fit through the biopsy channels of conventional endoscopes. It is, therefore, even more difficult to make an inherently larger and somewhat compliant coupling member for the transducer sufficiently small to pass through such biopsy channels. As a result, there has not heretofore been an acceptable solution for the problem of maintaining good acoustic coupling between endoscopically delivered transducers and internal tissues or organs.

DISCLOSURE OF THE INVENTION

It is an object of the invention to provide a miniature ultrasound imaging probe that is capable of achieving good acoustic coupling with internal tissues and organs.

It is another object of the invention to provide an acoustic coupling member that is sufficiently compact to easily fit through an endoscope biopsy channel yet is sufficiently large and compliant to provide an endoscopically delivered transducer with good acoustic coupling.

It is still another object of the invention to provide an acoustic coupling member for a miniature ultrasound imaging probe that provides the transducer with good acoustic coupling while it is being scanned over the surface of an internal tissue or organ.

It is a further object of the invention to provide an acoustic coupling member that can be used with a variety of endoscopically delivered ultrasound transducer designs.

These and other objects of the invention are provided by a miniature ultrasound imaging probe having a transducer mounted at the distal end of an elongated, flexible catheter adapted for insertion in an endoscope biopsy channel. The transducer includes a transducer body and an ultrasound transducer mounted in the body having a pair of conductors that extend through the catheter. The transducer includes a flexible bag sealingly surrounding the transducer body thereby isolating the transducer from the external environment. The interior of the bag is filled with an acoustic impedance matching fluid. The transducer also includes a mechanism for selectively altering the shape of the bag between first and second configurations. In its first configuration, the bag extends laterally away from the transducer body so that the bag can conform to a surface through which an image is to be obtained during use. In its second configuration, the bag extends longitudinally and has a reduced width to facilitate the insertion of the transducer through the endoscope biopsy channel.

The mechanism for selectively altering the shape of the bag preferably includes an actuator member coupled to the transducer body for moving the transducer body longitudinally with respect to the bag between first and second positions. In its second position, the transducer body pushes on the distal end of the bag and extends the bag along the sides of the transducer body. In its first position, the transducer body is retracted thereby allowing the bag to expand away from the transducer body so that it can conform to a curved or irregular surface.

The catheter preferably includes an outer tube to which the flexible bag is attached. The actuator member preferably includes an elongated shaft extending concentrically through the outer tube with the transducer body secured to its distal end.

Although a variety of techniques and structures can be used to secure the flexible bag to the outer tube, a rigid collar mounted on the outer tube may be used. The collar has an axial bore through which the shaft extends, and the flexible bag extends around the periphery of the collar. The bag can be secured around the collar by a flexible cylindrical clip extending around the bag and collar.

The probe may also include an axially slidable overtube extending along and surrounding the catheter. The overtube can be extended to surround the flexible bag when the probe is in the narrowed second position and is about to be inserted through the endoscope biopsy channel in order to protect the bag. The overtube is then retracted so that the flexible bag projects beyond the overtube in the first position when the probe is to be used for internal imaging.

A combination can also be used in which the bag is stretched by the transducer to elongate the bag, and the elongated bag is pulled into the overtube for protection during passage through the endoscope biopsy channel. The overtube is then retracted so the elongated bag is now outside the overtube. Finally, the transducer is pulled back, thereby allowing the bag to expand to a larger diameter shape better suited to conform to an irregular surface.

Rotational or linear scanning of the probe may be accomplished by either rotating or reciprocating the entire probe or by rotating or reciprocating the transducer body within the bag.

Although the inventive imaging probe has been described for use with gastrointestinal endoscopes, such as colonoscopes and sigmoidoscopes, it will be understood that it may also be used with other types of scopes, such as angioscopes, bronchoscopes, laparoscopes, and arthroscopes, or to investigate other structures by passing the probe into the body without an endoscope.

BRIEF DESCRIPTION OF THE DRAWINGS

FIG. 4 is a detailed cross-sectional view of the preferred embodiment of the inventive miniature ultrasound imaging probe.

BEST MODE FOR CARRYING OUT THE INVENTION

Figure 1:
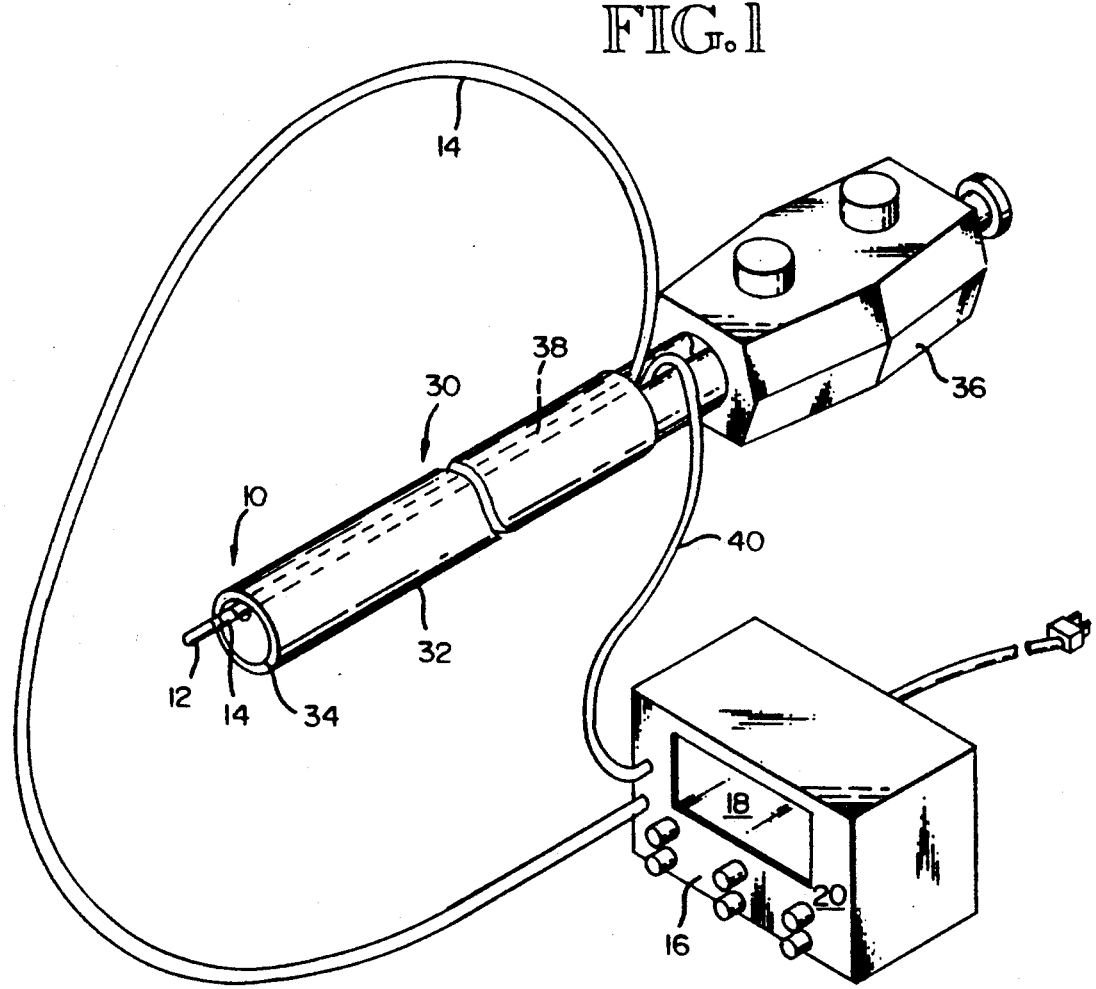
FIG. 1 is a schematic showing the preferred embodiment of the inventive miniature ultrasound imaging probe tip being used for internal imaging through an endoscope.

The inventive miniature ultrasound imaging probe is illustrated in use in FIG. 1. The probe 10 includes a probe tip 12 mounted at the distal end of an elongated flexible catheter 14 having its proximal end connected to an ultrasound imaging system 16. As is well known in the art, the ultrasound imaging system 16 includes a display 18 and a front panel 20 containing a variety of switches and selector knobs.

The ultrasound imaging probe 10 is used with a conventional endoscope 30 having an elongated, flexible insertion tube 32 terminating in a viewing tip 34 at its distal end and extending from a handle 36 at its proximal end. The endoscope 30, like virtually all endoscopes used for performing diagnoses and procedures, includes a biopsy channel 38 extending from the proximal end of the insertion tube 32 to the viewing tip 34. The biopsy channel 38 is conventionally used for threading diagnostic and therapeutic devices to the viewing tip 34 of the insertion tube 32 after the insertion tube 32 has been inserted into a body cavity of a patient.

In the case of the inventive ultrasound imaging probe 10, the probe tip 12 and catheter 14 are threaded through the biopsy channel 38 so that the probe tip 12 projects beyond the viewing tip 34 of the endoscope 30. By viewing through a window at the viewing tip 34 of the insertion tube 32, the probe tip 12 may be placed against tissues or an organ of which an image is to be obtained. The probe tip 12 is then scanned rotationally, linearly, or in some other manner, such as rocking, by rotating, reciprocating or otherwise moving the catheter 14 actuated from the proximal end. A conventional position transducer (not shown) in the handle 36 of the endoscope 30 provides a position output signal that is applied to the imaging system 16 through cable 40. The position output signal modulates one axis of the display 18 while the time delay of the ultrasound reflections via catheter 14 modulate the other axis of the display 18. The Z axis (i.e., intensity) of the display 18 is modulated by the intensity of the ultrasound returns.

The probe tip 12 can be placed against a surface of interest by advancing or rotating it or indirectly by manipulating the endoscope insertion tube 32. It is sometimes difficult to keep the probe tip 12 flush with the surface of interest. This problem is further exacerbated by the fact that the active surface of the probe tip 12 may not be exactly parallel with the surface of interest. Furthermore, the surface of interest may be curved or irregularly shaped. It is therefore difficult to maintain good acoustic coupling between the probe tip 12 and the surface of interest. It becomes even more difficult to maintain good acoustic coupling if the probe tip 12 slides along the surface of interest during rotational or linear scanning. The problem of maintaining good acoustic coupling is thus more acute for internal imaging than it is for imaging through external surfaces.

It is important for patient comfort that the diameter of the insertion tube 32 be as small as possible. It is for this reason that the diameter of the biopsy channel 38 must be fairly small. The maximum transverse dimension of the probe tip 12 must, of course, be less than the diameter of the biopsy channel 38. It is diffcult, but not impossible, to fabricate ultrasound transducers having acceptable performance that are narrow enough to fit through biopsy channels 38 typically found in conventional endoscopes. However, it is generally assumed by those skilled in the art that the need for a small transducer precludes the use of flexible, relatively bulky acoustic coupling devices such as used to provide good acoustic coupling for externally applied transducers. Thus, it is generally thought that acoustic couplers cannot be used for internal imaging.

Another approach to providing good acoustic coupling, namely using impedance matching gels, are also unsuitable for use in internal ultrasound imaging. Even if it was possible to line a surface of interest with a layer of acoustic coupling gel, it is generally not desirable for such gels to be taken internally.

It is also possible to inflate a balloon covering the transducer. However, this is not a viable technique because, in order to pass through the channel 38, the catheter 14 must have too small a diameter to easily contain a lumen for inflating the balloon. Also, a small diameter inflating lumen can cause bubbles to be generated in the fluid inflating the balloon. Bubbles would pose a serious problem in generating ultrasound images since the bubbles would reflect ultrasound energy. Thus, there is heretofore been no adequate technique for providing an endoscopically deliverable ultrasound transducer with good acoustic coupling.

Figure 2:
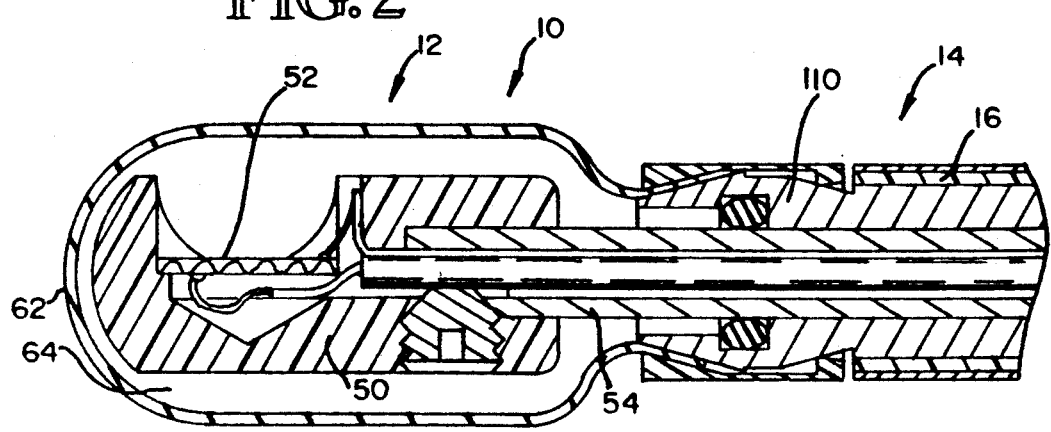
FIG. 2 is a schematic cross-sectional view of the preferred embodiment of the inventive miniature ultrasound imaging probe tip of FIG. 1.

The basic components of the miniature ultrasound imaging probe 10 are illustrated in FIGS. 2 and 4. The probe tip 12 includes a transducer body 50 carrying an ultrasound transducer 52. The transducer body 50 is mounted on the distal end of a hollow actuating rod 54 which is, in turn, mounted at the distal end of a triple wound, helical/anti-helical/helical spring 56. A coaxial cable 58 having a solid stainless steel outer shield 59 extends from the transducer 52 through the rod 54 and spring 56.

The rod 54 and spring 56 are surrounded by an outer tube 60. A flexible bag 62 surrounding the transducer body 50 is secured to the distal end of the collar 110, and the interior or the bag 62 is filled with an acoustic coupling fluid 64.

The bag 62 is fairly bulky, and the material forming the bag 62 is sufficiently compliant so that it can conform to curved and irregular surfaces. As a result, the bag 62 can be placed against a surface of interest and, since it will conform to that surface, it provides good acoustic coupling from the transducer 52 through the impedance matching fluid 64 and the surface of interest. However, since the bag 62 must be fairly bulky to carry out its intended function of conforming to curved and irregular surfaces, it unduly increases the width of the probe tip 12. It would therefore not seem feasible to utilize the configuration illustrated in FIG. 2 for applications requiring the probe tip 12 to be delivered through an endoscope biopsy channel.

Figure 3A:
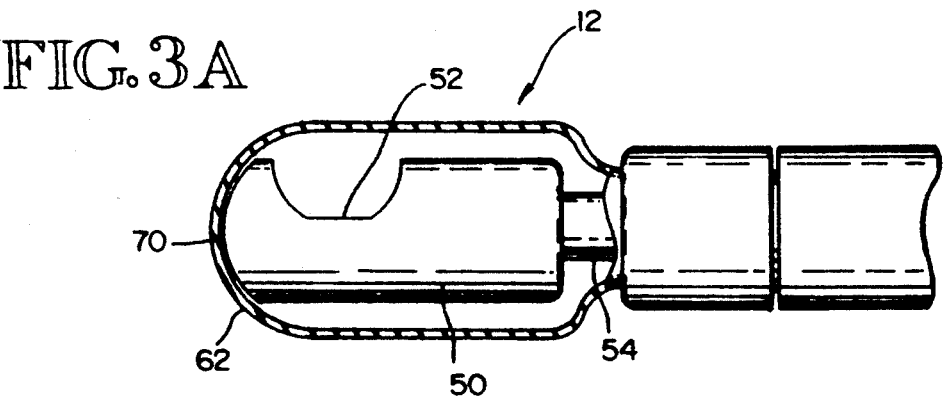
FIGS. 3A and 3B are schematics showing the operation of the miniature ultrasound imaging probe tip of FIG. 2.
Figure 3B:
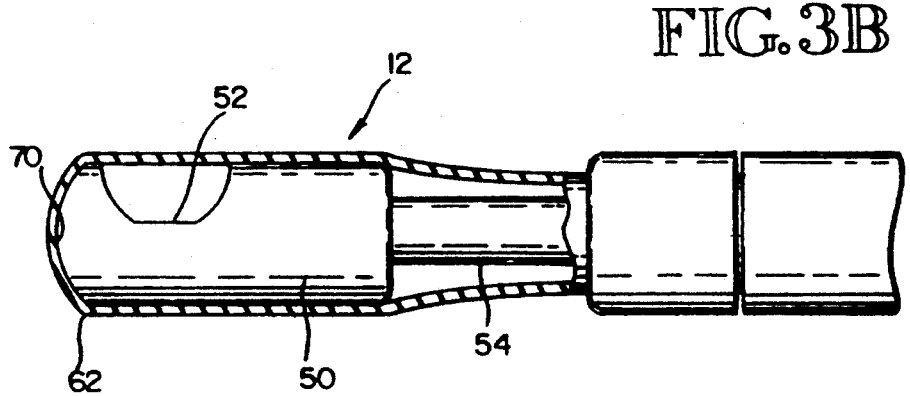

The inventive miniature ultrasound imaging probe illustrated in FIG. 2 is, however, capable of being inserted through endoscope biopsy channels by reconfiguring the shape of the bag 62, as illustrated in FIGS. 3A and 3B. The probe tip 12 is shown in FIG. 3A in the configuration it assumes when it is to be used for ultrasound imaging, as illustrated in FIG. 2.

It will be noted that the distal end of the transducer body 50 forms a curved surface 70 and that the width of the bag 62 is substantially larger than the maximum width of the transducer body 50. When the probe tip 12 is to be threaded through an endoscope biopsy channel, the rod 54 is extended, thereby extending the transducer body 50 so that its curved surface 70 contacts the distal end of the bag 62. As the transducer body 50 is extended further, it pushes against the distal end of the bag 62, thereby elongating the bag and causing it to conform to the periphery of the transducer body 50, as illustrated in FIG. 3B. In this configuration, the width of the probe tip 12 is reduced to substantially the width of the transducer body 50, and it may therefore pass through the endoscope biopsy channel as easily as the transducer body 50 alone. While the bag 62 is preferably somewhat resilient as well as flexible, it need not be resilient as long as it is flexible.

The structural details of the entire imaging probe 10 are illustrated in FIG. 4. As explained above, the probe tip 12 includes a transducer body 50 carrying the ultrasound tranducer 52. A bore formed in the proximal end of the transducer body 50 receives the distal end of a cylindrical actuating rod 54, hereinafter referred to as the distal actuating rod 54. A set screw 80 threaded through a radial bore in the transducer body 50 contacts the shield 59 of the coaxial cable 58 and prevents axial movement of the transducer body 50 with respect to the coaxial cable 58 and distal actuating rod 54. The proximal end of the distal actuating rod 54 terminates in a reduced diameter portion 82 which is surrounded by the spring 56. As explained above, the spring 56 is triple wound with helical, anti-helical, helical springs. The proximal end of the spring 56 surrounds a reduced diameter portion 84 of a cylindrical proximal actuating rod 86 which extends into an axial bore of an actuating member 90. The distal actuating rod 54, spring 56, and proximal actuating rod 86 are preferably formed from stainless steel. The spring provides the rotational shaft formed by the actuating rods 54, 86 and spring 56 with rotational strength and torque stability while the coaxial cable 58 provides the combination with axial strength.

The proximal actuating rod 86 is retained within the bore of the actuating member 90 by a set screw 92 that is threaded through a radial bore in the actuating member 90 to contact the coaxial cable 58. A pinion gear 94 is integrally formed with the actuating member 90. The coaxial cable 58 extends from the transducer 52 through the distal actuating rod 54, spring 56, and proximal actuating rod 86 to the actuating member 90. A center conductor 96 of the coaxial cable 58 is connected to an axial contact member 98 which terminates at a point 100 at the center of the pinion gear 94. The set screw 92 and actuating member 90 are fabricated from a conductive material, such as stainless steel. As a result, the conductive outer braid (not shown) of the coaxial cable 58 can make contact with a suitable contact (not shown) through the actuating member 90 and set screw 92. An insulator 160 is contained within the actuating member 90 to allow safe completion of the electrical circuit. The foregoing includes all of the components of the imaging probe 10 that are actuated to place the probe tip 12 in the configuration illustrated in FIG. 3B for passage through an endoscope biopsy channel and for scanning using the transducer 52.

The outer, relatively stationary elements of the ultrasound imaging probe 10 include the bag 62 as explained above. The opening of the bag 62 extends around a cylindrical collar 110 and is secured in place with a resilient, cylindrical clip 112. The collar 110 is clamped inside the distal end of the outer tube 60 by a conventional, stainless steel crimp ring 114. The outer tube 60 is preferably formed from a flexible, low-stick material such as Teflon. The bore of the collar 110 has formed therein an annular ring 120 which captures an O-ring 122 that contacts the outer surface of the distal actuating rod 54. The O-ring 122 seals the interior of the bag 62 to retain the impedance matching fluid 64 within the bag 62 while allowing the actuating rod 54 to rotate for scanning inside the bag 62 or for reorienting the direction of the transducer 52 inside the bag 62. The O-ring 122 seals the interior of the bag 62 to retain the impedance matching fluid 64 within the bag 62 while allowing the actuating rod 54 to move the transducer 52 longitudinally for either scanning linearly inside the bag or to extend the bag 62 so it can pass through a biopsy channel. It is also possible to scan by moving the entire probe 10 in a linear or a rocking manner with the bag 62 either stretched or relaxed into its increased diameter configuration.

The outer tube 60 is clamped to a reduced diameter portion of an adapter member 130 by a stainless steel crimp ring 132. The adapter member 130 is, in turn, secured inside a cylindrical member 136 by a pair of radially extending screws 138. The cylindrical member 136 slidably receives the actuating member 90. The actuating member 90 can, therefore, slide into the cylindrical member 136 to extend the proximal actuating rod 86, spring 56, and distal actuating rod 54 relative to the outer tube 60 in order to cause the curved surface 70 of the transducer body 50 to push against the distal end of the bag 62. The actuating member 90 can also be reciprocated in a linear manner to cause linear scanning of the transducer 52 although, by virtue of the pinion gear 94, it is specially adapted for rotational scanning inside the bag 62. If desired, scanning can be accomplished by rotating, rocking, or reciprocating the entire probe 10 by rotating, rocking, or reciprocating the cylindrical member 136 and actuating member 90 as a unit.

Although not necessary to the operation of the probe 10, the probe 10 may also include an overtube 150 that slidingly surrounds the outer tube 60. The proximal end of the overtube 150 is surrounded by and secured to an actuating collar 152. The purpose of the overtube 150 is to protect the bag 62 when it is being inserted through an endoscope biopsy channel. Accordingly, when the probe 10 is to be threaded through a biopsy channel, the actuating member 90 is first pushed into the cylindrical member 136 to cause the transducer body 50 to longitudinally extend the bag 62. The actuating collar 152 is then moved distally to cause the overtube 150 to slide along the outer tube 60 until it surrounds the bag 62. At this point, the actuating member 90 can be retracted out of the cylindrical member 136 and the overtube 150 will maintain the bag 62 in its narrow configuration. Once the probe tip 12 has been extended beyond the viewing tip 34 (FIG. 1) of the endoscope 32, the overtube 150 and actuating collar 152 are retracted to the position illustrated in FIG. 4 thereby allowing the bag 62 to resume its shape as shown in FIG. 3A. Finally, if the actuating member 90 has not previously been retracted with respect to the cylindrical member 136, the actuating member 90 is then retracted to place the bag 62 in its operating configuration as shown in FIG. 3A. When the probe 10 is to be removed from the endoscope biopsy channel, the above-described procedure is repeated.

The inventive ultrasound probe has been described as using a flexible bag 62 that is stretched by the transducer body 50 to reconfigure the shape of the bag 62 so that it can fit through the biopsy channel of a viewing scope. However, it will be apparent that the shape of a flexible bag can be reconfigured in other ways. For example, a magnet mounted in the distal end of the bag could be repelled by an electromagnet to longitudinally stretch the bag so that it can fit through a biopsy channel. Also, a narrow bag could be expanded to a configuration adapted to conform to irregular surfaces by increasing the pressure of the fluid in the bag though a variety of means, such as by actuating a piston. Thus, it should be understood that the invention is not limited to any specific technique for reconfiguring the bag 62.

It is thus seen that the inventive miniature ultrasound imaging probe allows a relatively bulky, compliant acoustic coupling member to be used with a miniature ultrasound transducer without unduly increasing the maximum transverse dimension of the transducer, thus allowing it to be used with conventionally sized endoscope biopsy channels.

We claim:

1. A miniature ultrasound imaging probe comprising:
   an elongated, flexible catheter adapted for insertion in a scope biopsy channel;
   a probe tip mounted on said catheter at its distal end, said probe tip including:
   (a) a transducer body;
   (b) an ultrasound transducer mounted in said body, said transducer having a pair of conductors extending through said catheter;
   (c) a flexible bag sealingly surrounding said transducer body thereby isolating said transducer from the external environment;
   (d) an impedance matching fluid surrounding said transducer and retained by said bag; and
   (e) conversion means for selectively altering the shape of said bag while maintaining the volume of the impedance matching fluid in said bag constant, said conversion means altering the shape of said bag between a first configuration in which said bag extends laterally away from said transducer body in at least one direction so that said bag can conform to a surface through which an image is to be obtained during use, and a second configuration in which said bag has a reduced width to facilitate the insertion of said probe tip through a relatively narrow passage.

2. The ultrasound imaging probe of claim 1 wherein said bag is altered into said second configuration by extending said bag longitudinally.

3. The ultrasound imaging probe of claim 1 wherein said bag is resilient to that it can be stretched when said transducer body is in said second position.

4. A miniature ultrasound imaging probe comprising:
an elongated, flexible catheter adapted for insertion in a scope biopsy channel:
a probe tip mounted on said catheter at its distal end, said probe tip including:
(a) a transducer body;
(b) an ultrasound transducer mounted in said body, said transducer having a pair of conductors extending through said catheter;
(c) a flexible bag sealingly surrounding said transducer body thereby isolating said transducer from the external environment;
(d) an impedance matching fluid surrounding said transducer and retained by said bag; and
(e) conversion means for selectively altering the shape of said bag between a first configuration in which said bag extends laterally away from said transducer body in at least one direction so that said bag can conform to a surface through which an image is to be obtained during use, and a second configuration in which said bag has a reduced width to facilitate the insertion of said probe tip through a relatively narrow passage, said conversion means including an actuator member coupled to said transducer body for moving said transducer body longitudinally with respect to said bag between a first position and a second position that is distal of said first position, said transducer body in said second position contacting the distal end of said bag and extending said bag along the sides of said transducer body to place said bag in said second configuration, said transducer body in said first position allowing said bag to expand away from said transducer body so that said bag can conform to a surface through which an image is to be obtained during use.

5. The ultrasound imaging probe of claim 4 wherein said catheter includes an outer tube to which said flexible bag is attached, and wherein said actuator member includes an elongated shaft extending concentrically through said outer tube so that said shaft can move longitudinally with respect to said outer tube, said transducer body being secured to the distal end of said shaft so that longitudinal movement of said shaft with respect to said outer tube moves said transducer body between said first and second positions.

6. The ultrasound imaging probe of claim 5 wherein said catheter further includes a tube adapted to be positioned at the entrance to said scope biopsy channel when said imaging probe is in use, and wherein said shaft includes a distal actuating rod carrying said transducer body at its distal end, a proximal actuating rod extending through said tube, and a multiple, oppositely wound spring extending through said catheter between said distal actuating rod and said proximal actuating rod so that longitudinal and rotational movement of said proximal actuating rod is coupled to said transducer body through said spring and said distal actuating rod.

7. The ultrasound imaging probe of claim 6 further including a pinion gear coupled to said proximal actuating rod to allow said proximal actuating rod to be rotationally driven thereby rotationally scanning said transducer body through said spring and said proximal actuating rod.

8. The ultrasound imaging probe of claim 7 wherein said pinion gear is integrally formed with said proximal actuating rod.

9. The ultrasound imaging probe of claim 7 wherein said proximal actuating rod includes an electrical contact positioned at the rotational axis of said proximal actuating rod, said electrical contact being connected to one of said conductors extending through said catheter so that the position of said electrical contact remains constant as said proximal actuating rod rotates.

10. The ultrasound imaging probe of claim 9 wherein said proximal actuating rod includes an electrically conductive portion connected to the other of said conductors extending through said catheter.

11. The ultrasound imaging probe of claim 5 wherein said outer tube includes a rigid collar having an axial bore through which said shaft extends, said flexible bag extending around the periphery of said collar, and wherein said imaging probe further includes a flexible cylindrical clip extending around said collar with said flexible bag therebetween thereby securing said flexible bag to said collar.

12. The ultrasound imaging probe of claim 11 further including an O-ring positioned between the inner bore of said collar and said shaft to seal the interior of said bag while allowing said shaft to move longitudinally with respect to said collar.

13. The ultrasound imaging probe of claim 12 wherein said O-ring is retained in an annular ring formed in the bore of said collar.

14. The ultrasound imaging probe of claim 4 wherein said transducer body has an outwardly curved distal end to that, when said transducer body is in its second position, said flexible bag has a smoothly curved distal end.

15. A miniature ultrasound imaging probe comprising:
an elongated, flexible catheter adapted for insertion in a scope biopsy channel;
a probe tip mounted on said catheter at its distal end, said probe tip including:
(a) a transducer body;
(b) an ultrasound transducer mounted in said body, said transducer having a pair of conductors extending through said catheter;
(c) a flexible bag sealingly surrounding said transducer body thereby isolating said transducer from the external environment;
(d) an impedance matching fluid surrounding said transducer and retained by said bag;
(e) conversion means for selectively altering the shape of said bag between a first configuration in which said bag extends laterally away from said transducer body in at least one direction so that said bag can conform to a surface through which an image is to be obtained during use, and a second configuration in which said bag has a reduced width to facilitate the insertion of said probe tip through a relatively narrow passage; and
an overtube extending along and surrounding said catheter, said overtube being axially slidable on said catheter so that said overtube can be moved to a first position in which said overtube surrounds said flexible bag when said probe is to be inserted through said scope biopsy channel, and to a second position in which said flexible bag projects beyond said overtube when said probe is to be used for internal imaging.

16. A miniature ultrasound imaging probe comprising:
   a transducer body;
   an ultrasound transducer mounted in said body;
   a flexible bag sealingly surrounding said transducer body thereby isolating said transducer from the external environment;
   an impedance matching fluid surrounding said transducer and retained by said bag; and
   an actuator moving said transducer body longitudinally with respect to said bag between a first position and a second position that is distal from said first position, said second position contacting the distal end of said bag and extending it along the sides of said transducer body to facilitate the insertion of said transducer through a relatively narrow passage, said first position allowing said bag to expand away from said transducer body so that said bag can conform to a surface through which an image is to be obtained during use.

17. The transducer of claim 16 wherein said transducer body has an outwardly curved distal end so that, when said transducer body is in its second position, said flexible bag has a smoothly curved distal end.

18. The transducer of claim 16 wherein said bag is resilient so that it can be stretched by said transducer body when said transducer body is in said second position.

19. A method of adapting an ultrasound imaging probe alternatively for insertion through a relatively narrow passage or for internal imaging, said probe having a probe tip mounted at the distal end of an elongated, flexible catheter, said probe tip having a ultrasound transducer, a flexible bag sealingly surrounding said transducer thereby isolating said transducer from the external environment, and an impedance matching fluid surrounding said transducer and retained by said bag, said method comprising selectively altering the shape of said bag between a first configuration and second configuration, in which the distal end of said bag extends longitudinally in a direction away from said catheter to elongate said bag, said bag in said first configuration extending laterally away from said transducer in at least one direction so that said bag can conform to a surface through which an image is to be obtained during use for internal imaging, and said bag in said second configuration having a reduced width to facilitate the insertion of said transducer through said scope biopsy channel.

20. The method of claim 19 wherein said shape of said bag is extended by pushing the distal end of said bag in an axial direction.

21. The method of claim 19 wherein said transducer is mounted in a transducer body, and wherein the distal end of said bag is pushed in an axial direction by moving said transducer body axially against the distal end of said bag.

22. The method of claim 21 wherein said bag is resilient, and wherein said transducer body stretches said bag when said transducer body moves axially against the distal end of said bag.

23. The method of claim 19 further including the step of rotating said transducer within said bag to rotationally scan during said internal imaging.

24. The method of claim 19 further including the step of moving said transducer in a linear manner within said bag to linearly scan during said internal imaging.

25. The method of claim 19 further including the step of rocking said transducer in an arcuate manner within said bag to scan during said internal imaging.

26. A method of adapting an ultrasound imaging probe alternatively for insertion through a relatively narrow passage or for internal imaging, said probe having a probe tip mounted at the distal end of an elongated, flexible catheter, said probe tip having a ultrasound transducer, a flexible bag sealingly surrounding said transducer thereby isolating said transducer from the external environment, and an impedance matching fluid surrounding said transducer and retained by said bag, said method comprising selectively altering the shape of said bag between first and second configurations, said bag in said first configuration extending laterally away from said transducer in at least one direction so that said bag can conform to a surface through which an image is to be obtained during use for internal imaging, and said bag in said second configuration having a reduced width to facilitate the insertion of said transducer through said scope biopsy channel, said method further including the step of selectively enclosing said flexible bag with a tube when said probe is to be inserted through said scope biopsy channel thereby protecting said bag.

* * * * *

UNITED STATES PATENT AND TRADEMARK OFFICE
CERTIFICATE OF CORRECTION

PATENT NO. : 5,178,150
DATED : January 12, 1993
INVENTOR(S) : Fred E. Silverstein and Andrew H. Proctor It is certified that error appears in the above-identified patent and that said Letters Patent is hereby corrected as shown below:

In column 1, after the subtitle "DESCRIPTION" and before "1. Field of the Invention" please add -- This invention was made with government support under grant number 5-R01-DK-34814-05 awarded by the National Institute of Health. The government has certain rights in the invention. -- .

Signed and Sealed this

Sixteenth Day of November, 1993

Attest:

BRUCE LEHMAN

Attesting Officer     Commissioner of Patents and Trademarks